United States Patent [19]

Faupel et al.

[11] Patent Number: 5,895,298
[45] Date of Patent: Apr. 20, 1999

[54] DC BIOPOTENTIAL ELECTRODE CONNECTOR AND CONNECTOR CONDITION SENSOR

[75] Inventors: Mark L. Faupel, Conyers; John Stephens; Seth D. Nathanson, both of Alpharetta, all of Ga.

[73] Assignee: Biofield Corp., Roswell, Ga.

[21] Appl. No.: 08/865,072

[22] Filed: May 29, 1997

[51] Int. Cl.[6] .................................................. H01R 4/48
[52] U.S. Cl. ............................ 439/729; 439/909; 439/859
[58] Field of Search .................................. 439/729, 819, 439/822, 859, 909, 910, 930, 268

[56] References Cited

U.S. PATENT DOCUMENTS

| | | | |
|---|---|---|---|
| 4,165,141 | 8/1979 | Williams et al. | 439/859 |
| 4,206,960 | 6/1980 | Tantillo et al. | 439/909 |
| 4,365,634 | 12/1982 | Bare et al. | 600/391 |
| 5,042,481 | 8/1991 | Suzuki et al. | 600/393 |
| 5,454,730 | 10/1995 | Tozuka | 439/910 |

*Primary Examiner*—Neil Abrams
*Assistant Examiner*—T. C. Patel
*Attorney, Agent, or Firm*—Sixbey, Friedman, Leedom & Ferguson; Daniel W. Sixbey

[57] ABSTRACT

An electrode connector and connector condition sensor for a biopotential sensing apparatus wherein a plurality of electrodes are connected to individual output leads for individual electrode channels by a connector which does not abrade the surface of the electrode button contact and does not require that pressure be applied to the electrode during connection. Two spring biased conductive arms for the connector are spread apart by the cam surface of an actuator button to receive the button contact and are contoured to engage substantially the entire peripheral surface of the button contact when the actuator button is released. The biopotential sensing apparatus includes a processor which senses the loss of signal in any electrode channel during a test period and activates an indicator to provide a warning indication.

17 Claims, 7 Drawing Sheets

DC BIOPOTENTIAL ELECTRODE CONNECTOR AND CONNECTOR CONDITION SENSOR

BACKGROUND OF THE INVENTION

The accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial volume of noise which makes accurate analysis difficult. Also, biological systems are notorious for their complexity, nonlinearity and nonpredictability, and wide variations from the norm are not uncommon. For example, DC biopotential signals tend to drift over time, so that if signals are not sensed and analyzed with some rapidity, signal errors due to drift occur.

For the accurate measurement of DC biopotentials for disease diagnosis and screening, electrode and electrode circuit characteristics and electrode placement become important. If an electrode ceases to make good contact with a subject during a measurement cycle, an erroneous indication may result.

Factors such as small DC offset potentials in the low millivolt range, which may have little effect on an AC biopotential measurement, such as ECG measurement, can destroy the accuracy of a DC biopotential measurement. For screening applications where many sensing electrodes are used, it is often critical for electrode characteristics to be uniform, for accurate electrode spacing to be maintained and for DC offsets to be substantially eliminated.

Many DC biopotential sensing electrodes are packaged in a pre-gelled state wherein an electrolytic paste or gel is packaged as part of the electrode. The gel may be located in a central gel reservoir consisting of a molded cup, or it may be contained in a dye-cut hole in a foam which encapsulates a gel saturated open cell compressible foam column. In most instances, the pre-gelled electrodes are sold ready for use with an electrically conductive material such as metal or a metal chloride in contact with the electrolyte gel.

A pre-gelled electrode system is generally not a battery by itself, but forms a part of a battery-system consisting of two or more electrodes placed on the body. In such a system, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC biopotentials are of interest, artifacts, such as DC offsets, should be reduced to the lowest level. Most pre-gelled electrodes when introduced in the battery system outlined above contribute some unwanted DC voltage (polarization effect) to biopotential measurements. It is important to lower the possibility of such DC artifacts occurring to a degree sufficient to preclude them from having a substantial adverse effect on biopotential measurements.

The design and performance characteristics for an effective DC biopotential electrode are different from those of electrodes designed for measuring alternating current (AC) signals such as those used with electrocardiology (ECG) and electroencephalography (EEG). For example, U.S. national standards for single use ECG electrodes allow the DC offset of an electrode pair (i.e., the spurious DC current generated by electrochemical interactions between electrode components) to be as high as 100 millivolts (ANSI/AAMI standard). Since effective use of DC signals for cancer diagnosis requires discrimination at the one millivolt level, standards for ECG electrodes are grossly excessive. ECG electrodes are intended for AC measurements which are not significantly affected by DC offset voltages in the electrode to the degree that DC biopotential measurements are adversely affected by such offset voltages. The traditional view taken in the manufacture of ECG pregelled electrodes is that to reduce DC offset, one must sacrifice AC impedance, and since a low AC impedance is most important in an ECG pregelled electrode, the DC offset voltage is tolerated. However, for highly accurate DC biopotential measurements, both the DC offset potential and the AC impedance for the electrode must be low.

If a pre-gelled electrode array is to be used effectively for disease detection, such as breast cancer screening, the array will require a relatively large number of spaced electrodes to cover substantially the entire surface of the breast. Not only must each of these electrodes be free from error causing offset potentials before use, but the electrodes must maintain contact with the curved surface of the breast without movement during the screening procedure and must maintain a predetermined array formation with specified electrode spacing. Consistent location and orientation of the electrical channels connected to the respective electrodes must also be maintained to prevent incorrect connection to the electrodes and to maintain positive contact between the electrodes and the electrical channel leads therefor.

The key to effective measurement and analysis of direct current skin potentials is absolute maintenance of signal integrity from the skin surface to the signal processing components of the measuring unit. This is especially critical due to the inherent low amplitude of biologic DC potentials. At any point in the electronic path from the skin sensing electrode to the measuring unit, potential exists for noise to intrude upon signal, thereby degrading diagnostically useful information.

In a DC biopotential sensing electrode, the connection between the electrode and the electrode lead which provides an output signal from the electrode to a measuring instrument is extremely important. Disposable DC biopotential electrodes normally include a sensor disc having a projecting button type connector with an enlarged head portion which is engaged by an electrical lead connector unit. To minimize the AC impedance of the electrode, the sensor disc and button connector are formed from a plastic body which is uniformly and entirely coated with a very thin layer of a conductive metal such as silver. This metal layer has a thickness within a range of 0.5 mil to 1.5 mil, and a break or disruption of this layer can degrade the DC biopotential sensed by the electrode.

Disposable medical electrodes normally are connected to an electrical lead by a snap connector in the form of a cup shaped female receptacle which is pressed downwardly over the button connector of the electrode sensor disc once the electrode is positioned on a subject. Although these snap connectors are effective when used with most A.C. disposable electrodes, such as ECG electrodes, they can be problematic when used with D.C. biopotential electrodes. With D.C. biopotential electrodes, a connector which is moved in engagement across the surface of the button connector during the connection process is likely to abrade or disrupt the thin conductive surface of the button connector during engagement. Also, since D.C. biopotential electrodes are presently used primarily for the detection of, or screening for breast cancer, the downward pressure required to engage a snap connector can cause pain or discomfort while also resulting in undesirable spreading of the electrode gel or electrolyte. Also, with snap connectors, patient movement can produce tension on the electrical lead from the electrode and movement or disengagement of the electrode from the skin of a subject.

DISCLOSURE OF THE INVENTION

It is a primary object of the present invention to provide a novel and improved electrode connector for a disposable biopotential electrode which provides a secure electrical connection with the button connector of an electrode sensor disc without creating pressure between the electrode and a patient.

Another object of the present invention is to provide a novel and improved electrode connector for a disposable biopotential electrode which provides a secure electrical connection with the button connector of an electrode sensing disc without moving over the surface of the button connector during engagement.

A further object of the present invention is to provide a novel and improved electrode connector for a disposable D.C. biopotential electrode which provides a secure electrical connection with the button connector of an electrode sensing disc by contacting substantially the entire circumferential surface of the button connector.

Yet a further object of the present invention is to provide a novel and improved electrode connector for a disposable DC biopotential electrode which can be connected and released by manually activating a release button without creating pressure between the electrode and a patient.

A still further object of the present invention is to provide a DC biopotential measuring unit for use with a biopotential electrode array which provides an interrupt indication during a measurement cycle if an electrode ceases to operate properly, becomes disengaged from a subject or an electrode connector becomes disengaged from an electrode.

DISCLOSURE OF THE PREFERRED EMBODIMENTS

Figure 1:
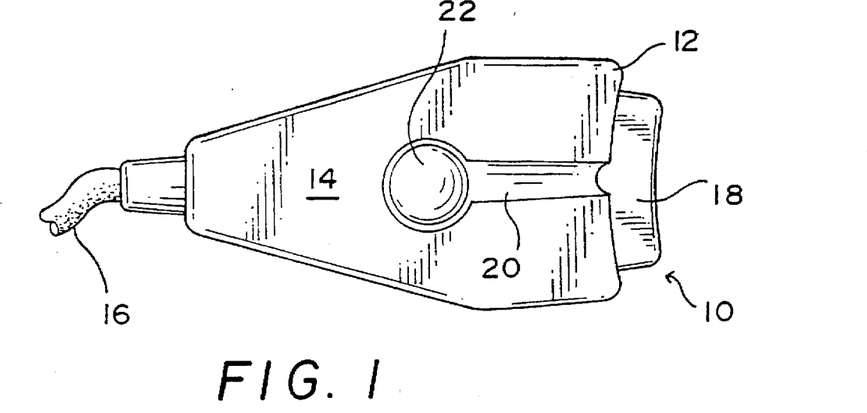
FIG. 1 is a bottom plan view of the DC biopotential electrode connector of the present invention.
Figure 2:
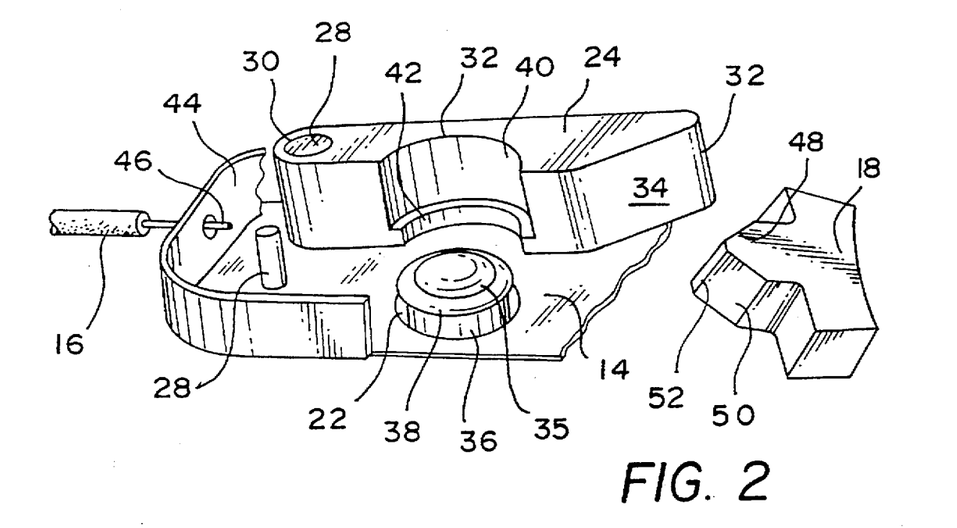
FIG. 2 is an exploded view of a portion of the DC biopotential electrode connector of FIG. 1.
Figure 3:
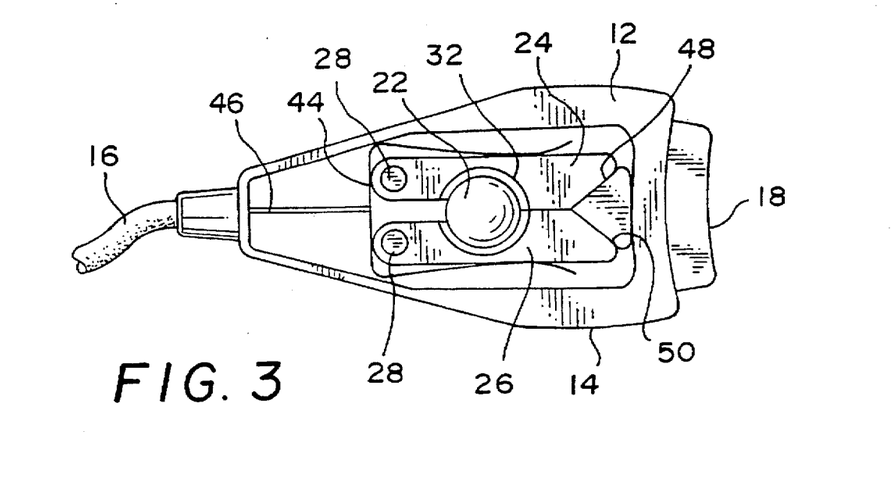
FIG. 3 is a sectional view of the DC biopotential electrode connector of FIG. 1.

Referring now to FIGS. 1–3, the DC biopotential electrode connector of the present invention indicated generally at 10 includes a housing 12 having a bottom wall 14. An electrical lead wire 16 extends outwardly from one end of the housing while an actuator button 18 extends outwardly from the opposite end of the housing. The bottom wall of the housing includes a channel 20 which extends from the end of the housing beneath the actuator button 18 to an opening 22 in the bottom wall 14 of the housing.

With reference to FIGS. 2 and 3, the operating mechanism for the DC biopotential electrode connector 10 which is enclosed by the housing 12 is shown. This mechanism includes first and second electrically conductive arms 24 and 26 which are pivotally mounted at an inner end to the housing 12. Two pivot posts 28 extend upwardly from the bottom wall 14 of the housing 12 into apertures 30 in the electrically conductive arms 24 and 26. These pivot posts mount the arms for pivotal movement relative to the housing.

The electrically conductive arms 24 and 26 are identical in construction and include an outer free end 32 including an inwardly inclined cam surface 34. Positioned substantially centrally of each of the electrically conductive arms is an arcuately contoured section 32 which is adapted to receive and engage the projecting button connector 35 of a DC biopotential electrode. These button connectors include a round shaft 36 which is of reduced diameter relative to an enlarged round head 38. When the button connector projects through the opening 22 in the housing bottom wall 14, the head of the button connector is engaged by an enlarged upper section of the arcuately shaped contoured section 32 while the shaft of the button connector is engaged by a projecting lower section 42 of the arcuately shaped contoured section 32 which is of reduced diameter relative to the enlarged upper section. The enlarged upper section is contoured to conform to the contour of the head 38 for the button connector 34 while the lower section 42 is contoured to conform to the outer contour of the button connector shaft. The arcuately shaped contoured sections 32 of the electrically conductive arms 24 and 26 are oppositely disposed over the opening 22 in alignment therewith.

Engaging the outer surfaces of the electrically conductive arms 24 and 26 is a U shaped leaf spring 44 which operates to bias the arms toward one another around the pivot posts 28. The lead wire 16 is soldered or otherwise retained within an opening 46 in the U shaped leaf spring 44 so that the lead wire is electrically connected to the leaf spring. Both the leaf spring and the electrically conductive arms 24 and 26 are highly conductive and operate to conduct very small DC biopotentials from the button connector 35 to the lead wire 16. Ideally, the leaf spring and the electrically conductive arms 24 and 26 are coated with a thin coating of a highly conductive metal which preferably is gold. Under the gold coating, the body of the leaf spring can be spring steel or a spring type plastic, while the body of each of the electrically conductive arms can be plastic or a metal such as stainless steel.

To operate the electrode connector 10, the actuator button 18 is mounted for movement inwardly of the housing 12. The inward end of the actuator button includes two cam surfaces 48 and 50 which incline outwardly from a central apex 52. The cam surfaces 48 and 50 are inclined to correspond with the incline of the cam surfaces 34 at the free ends of the electrically conductive arms 24 and 26. Normally, when the leaf spring 44 biases the electrically conductive arms together over the opening 22, the actuator button 18 will be forced outwardly from the housing 12 to its maximum projecting position shown in FIG. 1. However, when it is desired to attach the electrode connector 10 to a button connector 35, the actuator button 18 is depressed toward the housing 12, and the cam surfaces 48 and 50 engage the cam surfaces 34 and force the electrically conductive arms 24 and 26 apart as shown in FIG. 3. Now the space between the arcuately shaped contoured sections 32 is greater than that required to receive the button connector 35 so that the end of the button connector can pass by the lower section 42 of the arcuately shaped contoured sections 32. With the actuator button compressed, the housing 12 is placed over the button connector 35 for a DC biopotential electrode so that the button connector projects into the channel 20. Now the housing 12 is moved so that the button connector is guided down the channel 20 and into the opening 22. This can be done without applying pressure to the button connector, and since the channel 20 provides a guide for the button connector directly to the opening 22, the button connector can be passed in through the opening with no pressure being applied to the button connector and its associated electrode. Once the button connector has passed in through the opening 22, the actuator button 18 can be released and the bias of the spring 44 will pivot the electrically conductive arms toward one another about the pivot posts 28 while forcing the actuator button outwardly of the housing 12. Now the lower section 42 of the arcuately shaped contoured section 32 will pass under the head 38 of the button connector and engage the shaft 36 while the enlarged upper section 40 will engage the head 38. The arcuately shaped contoured sections 32 of the arms 24 and 26 are formed to engage substantially the entire periphery of the shaft and head of the button contact 35 so that extremely good electrical contact is made. To release the electrode connector 10 from the button connector 35, the actuator button 18 is again depressed to spread the electrically conductive arms 24 and 26 so that the electrical connector can be lifted away from the electrode.

The entire housing 12 or at least a portion of the housing wall opposite to the bottom wall 14 is made of transparent plastic or similar material so that application of the connector 10 to the button contact 35 can be visually monitored.

Figure 4:
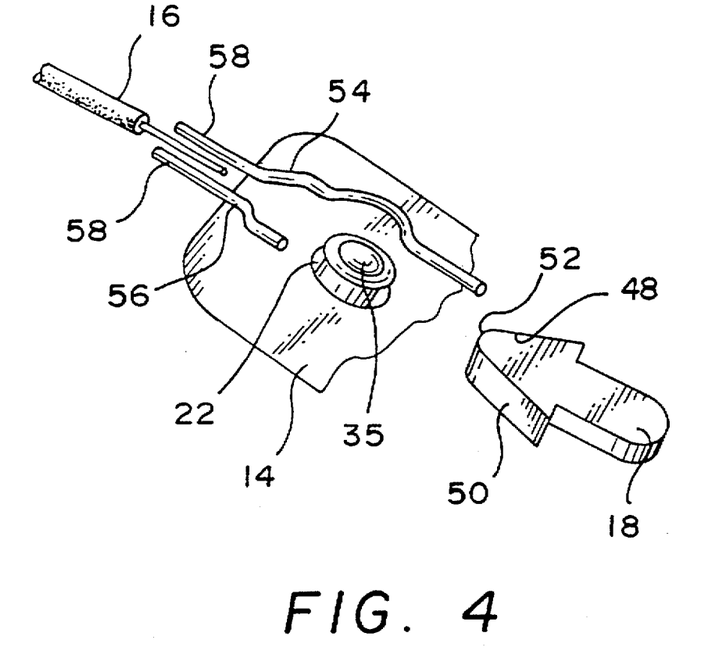
FIG. 4 is an exploded view of a portion of a second embodiment of the DC biopotential electrode connector of the present invention.
Figure 5:
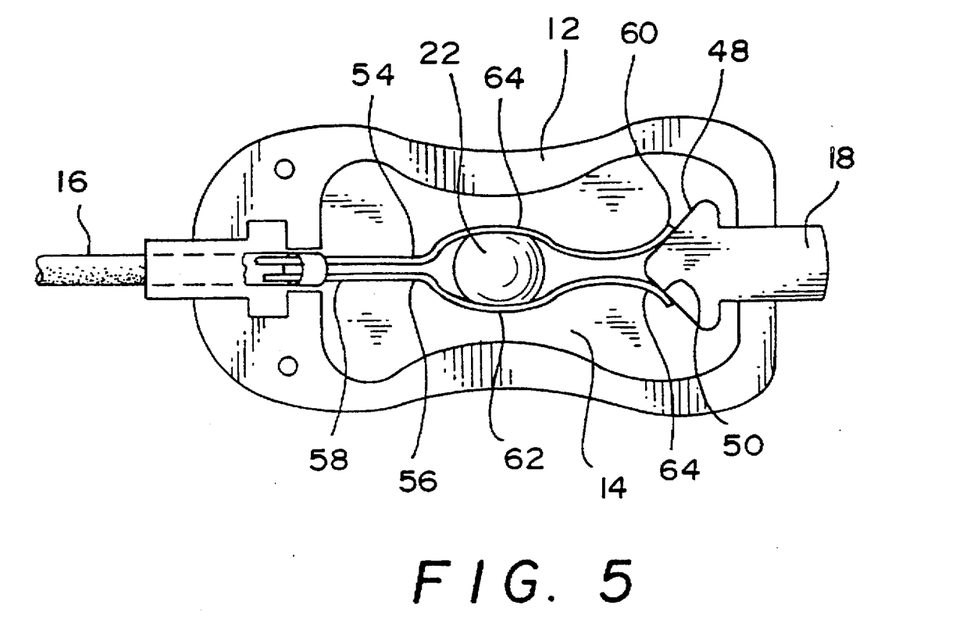
FIG. 5 is a sectional view of the DC biopotential electrode connector of FIG. 4.

FIGS. 4 and 5 disclose a second embodiment of the electrical connector 10 wherein the leaf spring 44 and the electrically conductive arms 24 and 26 are replaced by two conductive spring wires 54 and 56. These spring wires are formed of gold coated steel spring material or other suitable conductive spring material which would operate to conduct low DC biopotentials to the lead wire 16. The conductive spring wires 54 and 56 provide spring biased conductive arms having inner ends 58 which are secured to the lead wire 16. Each of the spring wires has a free end 60 which is angled outwardly at 62 to provide a cam surface for engaging the cam surfaces 48 and 50 of the actuator button 18. Formed substantially centrally of each of the conductive spring wires is an arcuately contoured section 62 which is aligned with the opening 22 in the housing bottom wall 14. These arcuately contoured sections engage and substantially surround the entire periphery of the shaft 36 of the button connector 35 and are contoured to conform to the outer contour of the button connector shaft.

The conductive spring wires 54 and 56 operate in the same manner as the spring biased electrically conductive arms 24 and 26 of FIGS. 1–3. When the actuator button 18 is depressed toward the housing 12, the cam surfaces 48 and 50 engage the cam surfaces 62 and spread the conductive spring wires 54 and 56 apart over the opening 22. Now the button connector 35 can be inserted through the opening 22 between the conductive spring wires and the actuator button 18 is then released to allow the spring wires to spring back against the shaft 36 of the button connector.

Figure 6:
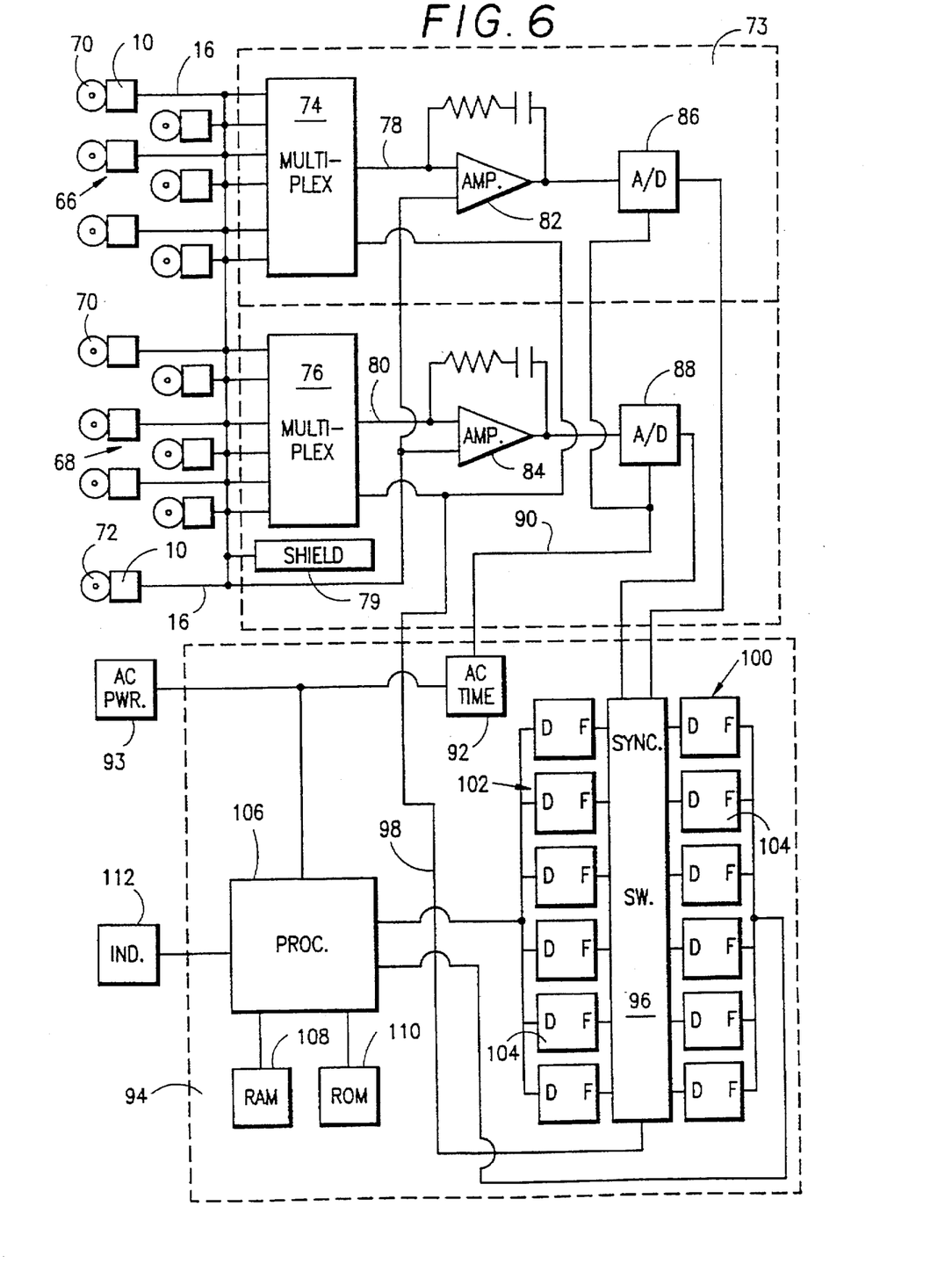
FIG. 6 is a block diagram of a DC biopotential measuring unit for use with the DC biopotential electrode connector of the present invention.

To test or screen a patient for a disease condition using DC biopotentials, a multiple electrode array is positioned on the patient, and each electrode can then be connected to a measuring device by the electrode connectors 10. It is sometimes possible due to patient movement to place stress on a lead wire 16 causing an electrode to either lose contact with the patient or become disconnected from the electrode connector 10. In a DC biopotential measuring system which performs a discriminant analysis to obtain a differential signal indicative of the presence, absence, or state of a condition at a test site on a human or animal subject, it is extremely important that each electrode in the test array maintain contact with the patient and remain connected to its respective lead wire 16 throughout the test. FIG. 6 illustrates a biopotential measuring system which senses when an electrode ceases to provide a signal during a test period and provides an indication so that the test period may be terminated and reinitiated after the electrode is reconnected.

In FIG. 6 for purposes of illustration, two electrode arrays 66 and 68 are shown with each array consisting of electrodes 70 and separate lead wires providing a separate output channel, one for each electrode in each array. In actual practice, each array can contain more electrodes and more than two arrays can be employed.

The electrodes 70 of the electrode arrays 66 and 68 should be mounted in a manner which permits the electrodes to be accurately positioned against the curved surface of the skin of a subject in the area of a test site while still maintaining uniform spacing and the position of the electrodes in a predetermined pattern. The electrodes 70 and at least one reference electrode 72 must all be of a type suitable for detecting DC biopotentials indicative of the potential level of the electromagnetic field present in a living organism. These electrodes should be of a type which does not cause a substantial battery effect between the organism under test and the electrodes and must have both a very low DC offset potential and a low AC impedance.

The DC biopotential measuring device is a multi-channel device having electrode leads 16 connected by electrode connectors 10 to the electrodes 70 in each array and an electrode lead 16 connected by a connector 10 to the reference electrode 72. Each electrode in combination with the reference electrode forms a separate data channel which transmits a plurality of analog signals indicative of the DC biopotentials at a specific site in a test area to one or more analog circuits 73. The electrode leads 16 from the array 66 are connected to a solid state multiplexor 74 such as a Harris Semiconductor Model HI-546-5, while the electrode leads from the electrode array 68 are connected to a second solid state multiplexor 76 in a manner to be subsequently described. Each electrode array provides a plurality of outputs to a multiplexor connected to the array, and this multiplexor switches between the individual electrode leads 16 during a test period to connect the analog signals on each lead sequentially to a multiplexor output such as the output lines 78 and 80 to create a time division multiplexed output. By dividing the electrodes 70 into a plurality of arrays and by providing a high speed solid state multiplexor for each array, it is possible to repeatedly sample biopotentials from a large number of electrodes during a test period of minimal duration.

The electrode leads 16 are also connected to a shielding circuit 79 in the analog circuit 73 to provide cable interface noise cancellation.

The analog signals on the outputs 78 and 80 from each multiplexor are passed through separate relatively higher frequency low pass filter amplifiers, such as the filter amplifiers 82 and 84. These filter amplifiers have a relatively high cutoff frequency of 40 Hertz or more, and thus require a short stabilization period with analog signals of the amplitude provided on the output lines 78 and 80 to the filters.

The analog output signals from the filter amplifier 82 connected to the multiplexor for the electrode array 66 are directed to an analog to digital converter 86, while the analog output signals from the filter amplifier 84 for the electrode array 68 are connected to an analog to digital converter 88. The analog to digital converters operate to convert the input analog signals to output digital signals which are a function of the analog inputs.

The analog to digital converters 86 and 88 operate in response to timing signals provided on a timing line 90 from a timer section 92 of a digital processor unit 94 which synchronize the conversions with the line frequency of the AC power 93 for the system. The electrical digital signals from the analog to digital converters are directed to a synchronous switching or de-multiplexor 96.

The de-multiplexor 96 is synchronized with the multiplexors 74 and 76 and provides timing signals on a line 98 to the multiplexors. Digital filter arrays 100 and 102 in the software for the digital processor unit include a dedicated digital filter 104 such as two-pole, Infinite Impulse Response (IIR) filter, with a Butterworth response, for each electrode and electrode channel in the electrode arrays 66 and 68 respectively. Thus, as the multiplexors 74 and 76 are simultaneously transmitting analog signals from a selected electrode channel in the electrode arrays 66 and 68, the digital signals indicative of these analog signals are being directed by the de-multiplexor to the digital filters 104 in the arrays 100 and 102 which are dedicated to those channels. When the multiplexors switch channels, the de-multiplexor switches to corresponding digital filters.

Filtered digital data from the digital filter arrays 100 and 102 are directed to processing section 106 of the digital processor unit 94 having a RAM memory 108 and a ROM memory 110. This data is stored by channel in memory and is processed by the processing section in accordance with a stored program to perform the condition screening or sensing functions of the present invention. An output from the processing section is connected to control the display on an indicator unit 112.

In the event that an electrode 70 ceases to operate properly or becomes disconnected from a patient or from the electrode connector 10 during a test period, the processing section senses the absence of an acceptable signal including the total absence of a signal from the digital filter 104 for that electrode and signals the indicator 112 to provide an indication warning. This indication may also include an identification of the faulty electrode since each digital filter 104 is dedicated to a specific electrode. The warning indication will alert an operator to terminate the test, check the faulty electrode and initiate a new test procedure.

Should the reference electrode 72 become disconnected, the signal on all channels using this reference electrode will be terminated and the processing section will sense this lack of signal as the de-multiplexor 96 switches between filters. Upon the reception of no signal on a plurality of channels, the processing section will signal the indicator to indicate that a reference electrode is loose.

It should be understood that for clarity of description, sections of the central processor unit 94 have been illustrated as operative blocks, but these sections may constitute software controlled functions.

The operation of the apparatus of FIG. 6 will be clearly understood from a brief consideration of the steps which the device is intended to perform. The electrode arrays 66 and 68 are positioned over various diverse areas of a test site, and the reference electrode 72 is then brought into contact with the skin of the subject in spaced relationship to the electrode arrays. This reference electrode might, for example, be brought into contact with a hand or sub-xyphoid area of the subject. The electromagnetic field between the reference electrode and each of the electrodes 70 is measured, converted to a digital signal and stored for processing by the processing section 94. The program control for the central processor unit causes a plurality of these measurements for each channel (i.e. 150) to be taken repetitively, and the measurements on all channels are taken sequentially during a predetermined test period. Sequential measurements between the reference electrode and one of the electrodes 70 in each array 66 and 68 are taken until each channel is sampled, and then the sequential measurement is repeated throughout the duration of the predetermined test period. The stored measurement indications from each individual channel are not averaged with those from other channels, but are instead kept separate and averaged by channel within the processing section 106 at the end of the test period. For the duration of a single test period, for example, from twelve measurement channels, the processing section will obtain twelve average signals indicative of the average electromagnetic at field for the test period between the reference electrode 72 and each of the electrodes 70 in the electrode arrays 66 and 68. Of course, more reference electrodes can be used, although only one reference electrode has been shown for purposes of illustration.

Having once obtained a final average signal level indication for each channel, the results of the measurements taken at multiple sites are analyzed mathematically to determine the relationships between the average signal values obtained. It has been found that the result of such an analysis is that a subset of relationships can be obtained which are indicative of the presence of more serious disease, injury or other conditions, while a different subset might be obtained which will be indicative of the absence of such conditions.

One of the most important relationships to be obtained is the maximum voltage differential (MVD), which is defined as the minimum average voltage value obtained during the test period subtracted from the maximum average voltage value obtained for the same period where two or more electrodes are recording DC potentials from a test site. Thus, for each predetermined test period, the lowest average voltage level indication obtained on any of the channels is subtracted from the highest average voltage level indication obtained on any of the channels to obtain an MVD voltage level. If this MVD voltage level is above or below a desired level >x, then a disease condition, such as a malignancy, injury or other condition could be indicated.

Since the contribution of each electrode channel is important in obtaining an accurate maximum voltage differential at the end of the test period, the test period should be terminated and a new test period initiated if an electrode 70 ceases, during the test period, to provide an acceptable signal. Otherwise an erroneous average will be obtained for that electrode channel, and this average may well result in an erroneous MVD reading.

Figures 7, 8:
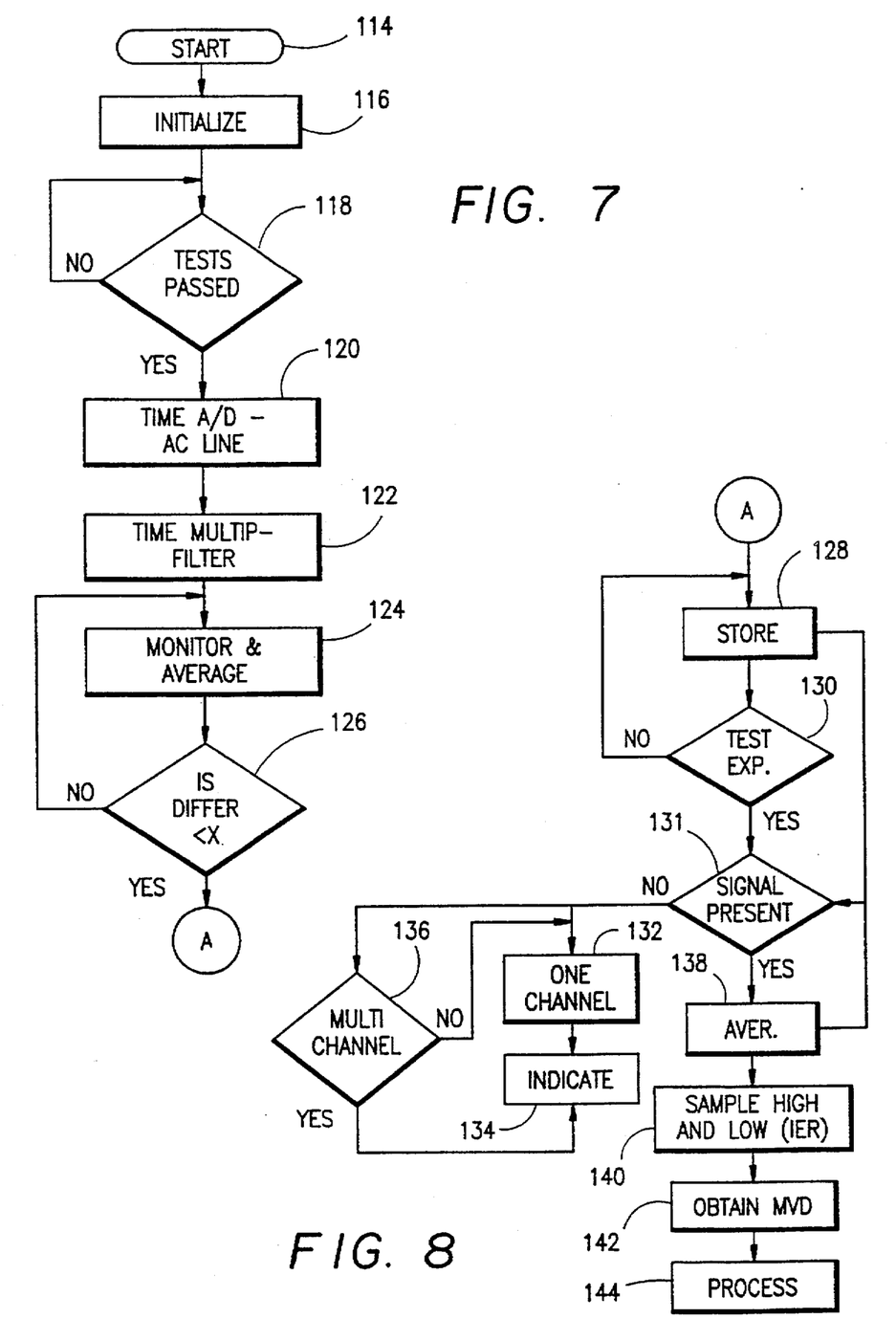
FIGS. 7 and 8 are flow diagrams illustrating the operation of the central processor of FIG. 6 to indicate a loose or disconnected electrode.

The general overall operation of the central processing unit will best be understood with reference to the flow diagrams of FIGS. 7 and 8. The operation of the measuring unit is started by a suitable start switch as indicated at 114 to energize the central processing unit 94, and this triggers an initiate state 116. In the initiate state, the various components of the device are automatically brought to an operating mode, with for example, the indicator 112 being activated while various control registers for the central processing unit are reset to a desired state.

Subsequently, a functional test period is initiated at 118 wherein the various components of the system are tested for proper operability. During this functional test period, the electrode arrays 66 and 68 may also be tested to make certain that electrodes are being used which accurately measure DC biopotentials.

If all system components test out properly during the system functional test period, then timing of the analog to digital converters in accordance with the AC line frequency begins at 120 and the timing of the multiplexors and de-multiplexors begins at 122. With the analog to digital converters, multiplexors, de-multiplexors and digital filters in operation, it is now possible to monitor the biopotential signals from a test area during a monitoring period begun at 124. During this monitoring period, conditions in the test area contacted by the electrode arrays 66 and 68 are stabilized so that subsequent reliable measurements of DC biopotentials can be obtained. Since the stabilization period for different subjects varies, some unknown time period must lapse before reliable measurements of DC biopotentials are obtained. Thus, at 124, a predetermined monitoring period is initiated, and the signals on all channels are monitored and averaged. Then, at the end of the initial monitoring period, the individual signals are compared at 126 to the average to obtain a value indicative of the relationship therebetween, and if this relationship value is greater than a predetermined value x, then sufficient signal stabilization has not occurred during the monitoring period and a new monitoring period is initiated. Conversely, if the relationship values obtained are less than the predetermined value x, then the monitoring period is terminated and a test period is initiated at A. Alternatively, the monitoring period can be an extended time period, for example, ten minutes, which is used for all patients and is sufficient to insure signal stabilization.

With reference to FIG. 8, once a test period is initiated, individual electrode channels are sequentially accessed and a number of test potentials (i.e. 150) are taken for each channel, digitized, filtered and stored by channel at 128. When the test period expires at 130, each stored channel of data is monitored at 131 to determine whether or not stored signals are missing on one channel, the channel is identified at 132 and a warning indication with an identification of the electrode involved based on the channel identification is provided at 134. If signals are absent from multiple channels, this is identified at 136 and a multiple channel indication is provided at 134. A multiple channel indication may evidence that a reference electrode is loose.

Once acceptable measurement values are determined to be present on all channels, a final average value for each channel is derived from the remaining measurements taken during the span of the test period at 138, and from these average values, the highest and lowest average value obtained within or between channels during the test period is sampled at 140. The lowest average channel value is subtracted from the highest average channel value at 142 to obtain a maximum voltage differential value. This maximum voltage differential value is then processed at 144 to indicate the presence or absence of a disease, injury, or other bodily condition, and during processing, can be compared with previously obtained differential values to determine the efficacy of treatment or the progress of a disease, injury or other bodily condition. The differential value may also be used to indicate the occurrence of a number of normal bodily functions such as ovulation, and normal or abnormal labor conditions.

Figure 13:
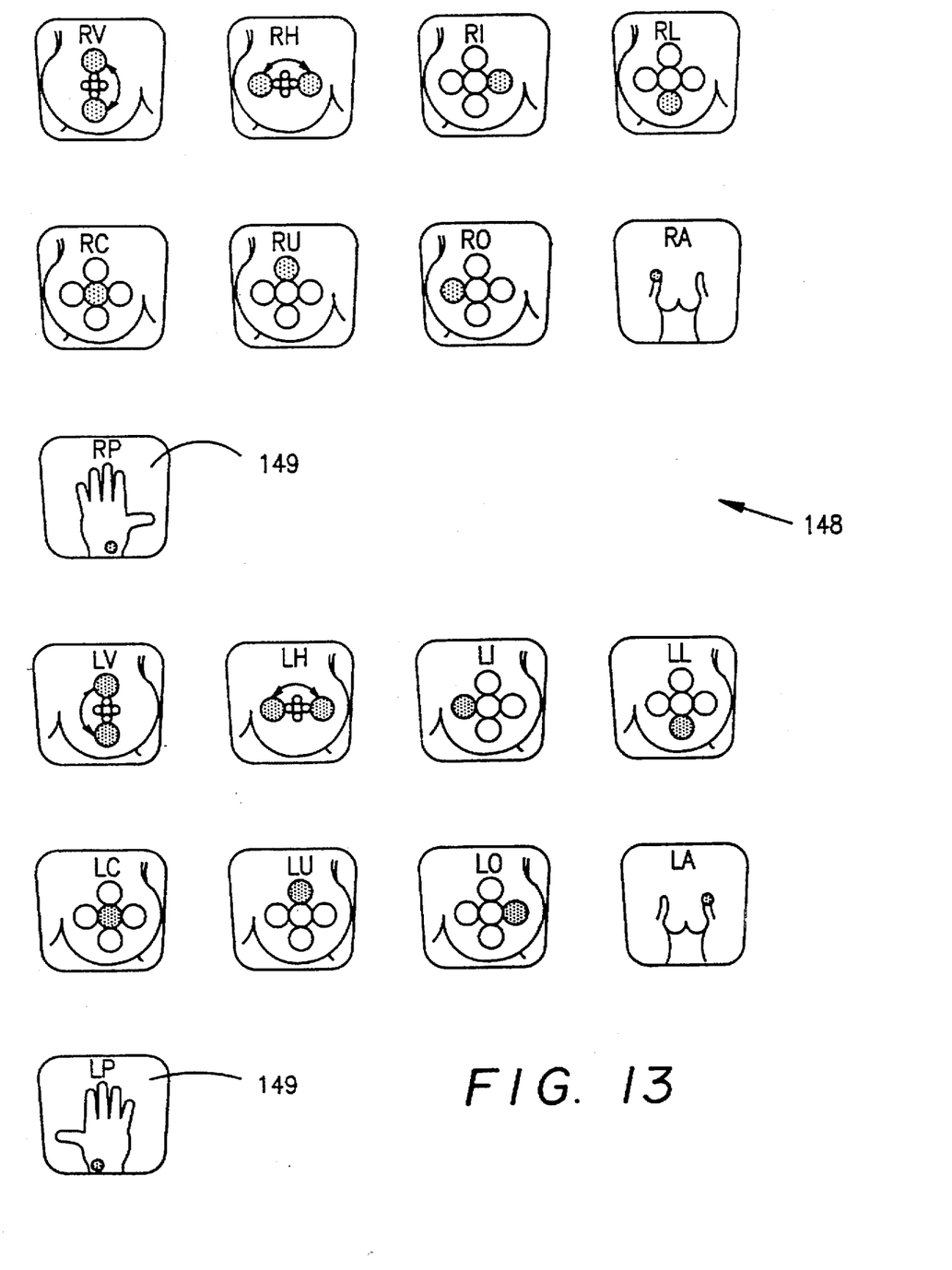
FIG. 13 is a plan view of the pictorial icons for the electrode connectors for the cable system of FIG. 9.

With reference to FIGS. 9–12, the electrode connectors 10 with their electrical leads 16 are components of a detachable cable system 146. Each of the connectors 10 bears a pictographic icon 148 which identifies where the associated electrode 70 or 72 is to be placed on a body relative to the remaining electrodes. The icon may also bear identifying letters, and when electrodes are placed in opposite sides of a body, the letters begin with "L" for the left side electrodes and "R" for the right side electrodes. Icons for left and right breast sensing electrode connectors are shown in FIG. 13 with the icons 149 designating the connectors for the reference electrodes.

The leads 16 for the right side electrodes extend through a right side yoke 150 while the leads 16 for the left side electrodes extend through a left side yoke 152. From the yokes 150 and 152, these leads extend through cables 154 and 156 to a commercially available, locking type zero insertion force connector 158. This connector has separate, individual connection terminals 160 numbered and lettered in FIGS. 11 and 12 for each lead 16 as well as connection terminals for shielding leads 162. The separate connection terminals 160 of the connector 158 mate with the separate terminals of a contact connector which provides separate channel electrical connection to the multiplexors 74 and 76. Also the contact connector connects the shielding leads 162 to the shielding circuit 79.

Figures 9, 10:
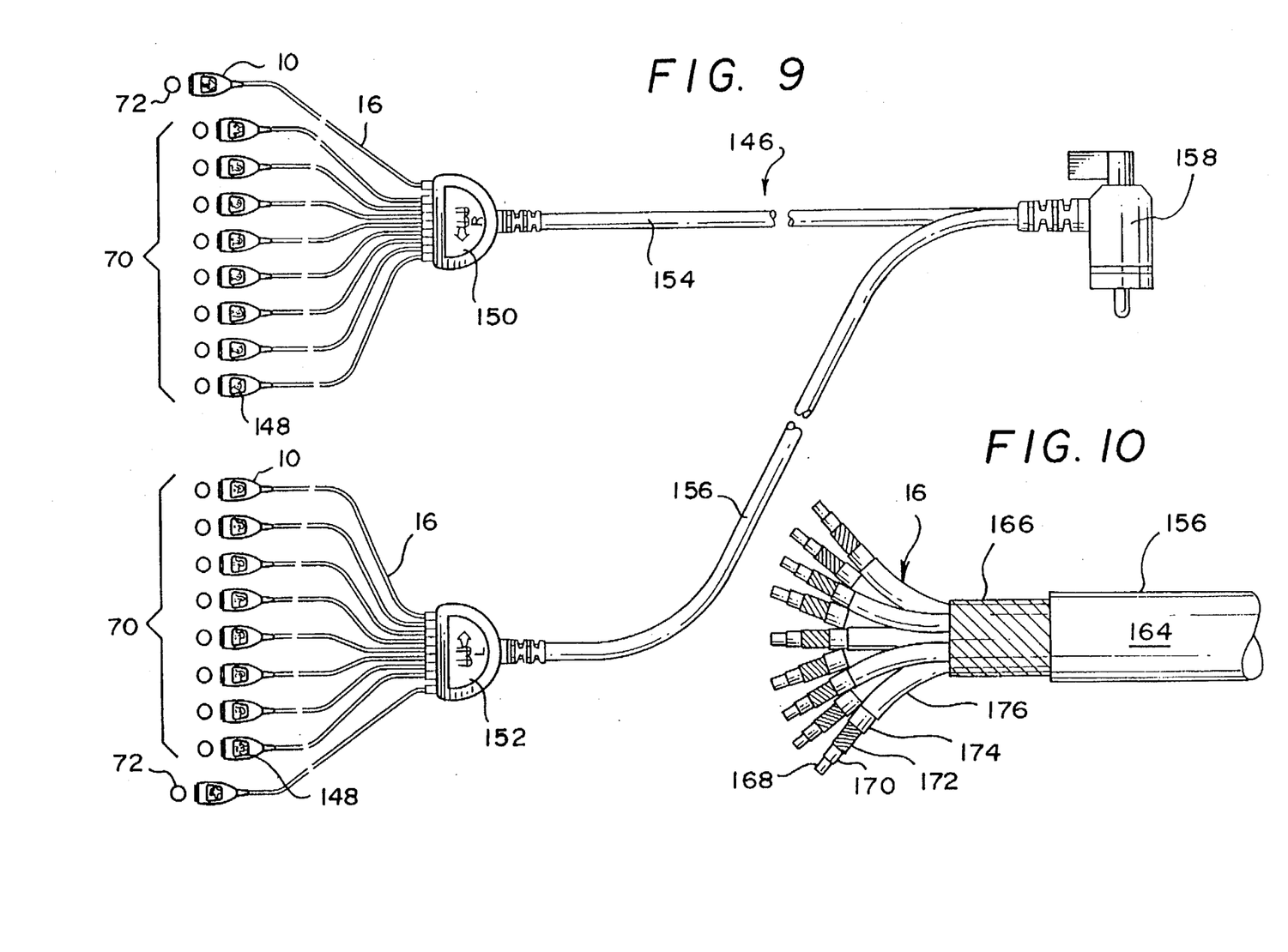
FIG. 9 is plan view of a cable system including DC biopotential electrode connectors of the present invention.
FIG. 10 is a partially sectioned view of the cable for the cable system of FIG. 9.

Referring now to FIG. 10, the cables 154 and 156 are identical in structure and their structure will be described with relation to the cable 156. Each cable includes a flexible outer jacket of insulating material 164, such as polyurethane with a paper separator wrap 166 under the outer jacket. This paper separator wrap surrounds the leads 16 which pass through the cable. Each of the leads 16 includes an electrical conductor 168 surrounded by an electrical insulating inner connector jacket 170, which is in turn encased in a tinned copper shield 172. A paper wrap 174 is provided around the tinned copper shield and this is covered by an insulating conductor outer jacket 176.

Figures 11, 12:
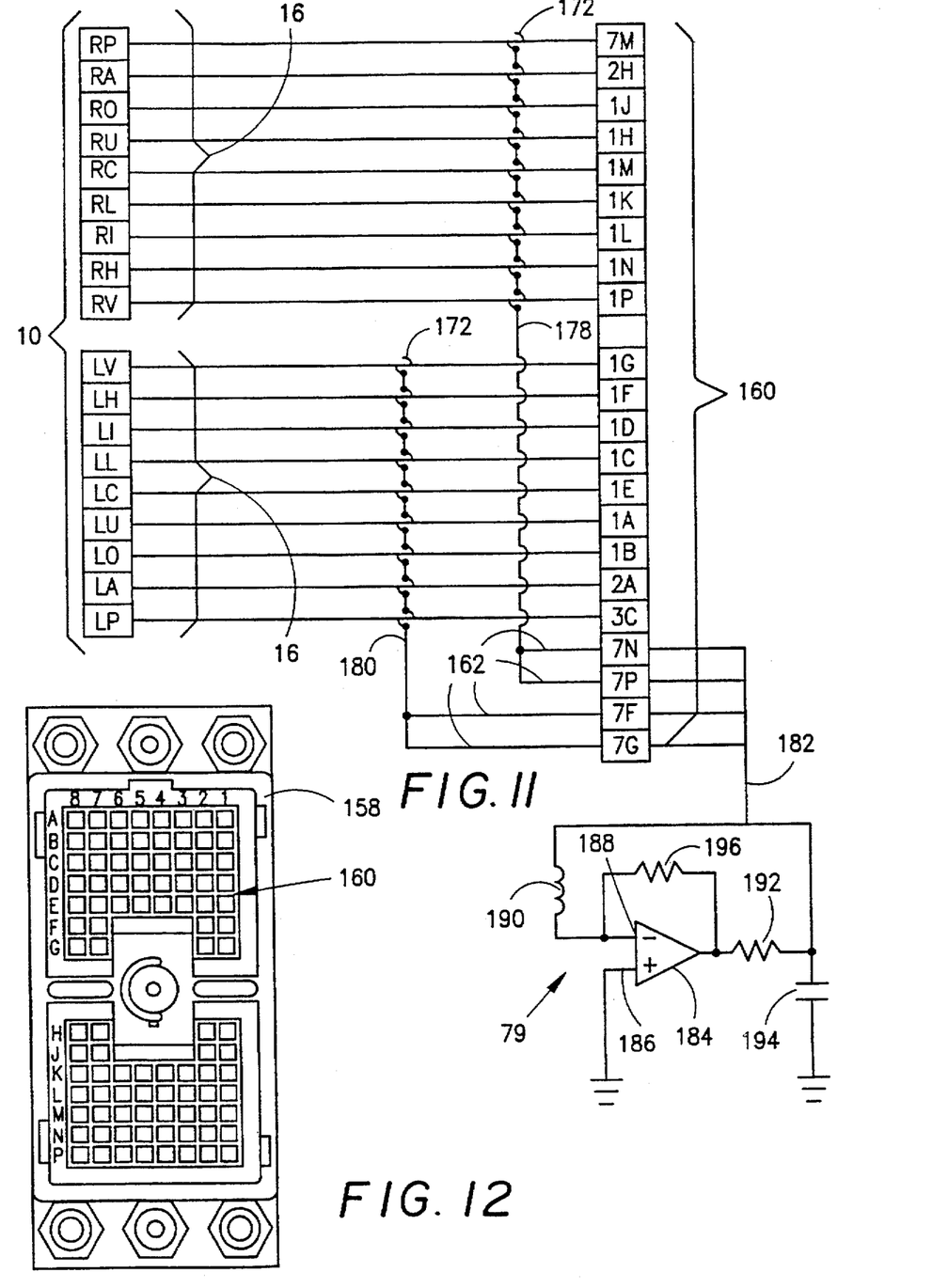
FIG. 11 is a circuit diagram of the shielding circuit for the cable system of FIG. 9.
FIG. 12 is a view in end elevation of the connector for the cable system of FIG. 9.

With reference to FIG. 11, the tinned copper shields 172 of each of the electrical leads 16 are electrically connected by leads 178 and 180 to the shielding leads 162, and when the cables 154 and 156 are connected to the analog circuit 73, these shielding leads are connected to the shielding circuit 79. This shielding circuit includes an input 182 connected across an operational amplifier 184 having a grounded reference input 186. The input 182 is connected to a signal input 188 of the operational amplifier by an inductor 190, and the output of the operational amplifier is connected by means of a resistor 192 and a capacitor 194 to ground. A resistor circuit 196 provides a short circuit between the signal input 188 and the output side of the operational amplifier 184.

Since the leads 16 carry very low volume DC biopotential signals in the one to ten millivolt range, it is critical that they be shielded so that these DC signals are not degraded by cable interface noise. The shielding circuit 79 operates effectively to cancel cable interface noise. It operates to vary the impedance to ground in response to increased noise.

We claim:

1. An electrical connector for electrically and mechanically interfacing with the peripheral surface of a projecting button connector for a biopotential electrode having an enlarged head connected to said electrode by a shank of reduced cross section relative to said head, said electrical connector comprising:

- a connector housing defining an enclosed inner chamber, said housing having an inner end and an outer end spaced from and opposite to said inner end, a housing top wall extending between said inner end and said outer end and a housing bottom wall spaced from said housing top wall and extending between said inner end and said outer end,
- first and second opposed, spring biased arms mounted on said connector housing within said inner chamber adjacent to the inner end of said connector housing, each of said arms having a free end section adjacent to the outer end of said connector housing which is movable toward and away from the free end section of the remaining arm, and
- an actuator mounted on said connector housing at the outer end there of which extends outwardly from said outer end and which includes an actuator section which engages and extends between the free end sections of said first and second spring biased arms, said actuator being mounted for movement relative to said connector housing toward and away from the inner end there of between a first position defining the outermost extent of actuator movement away from the inner end of said connector housing and a second position closer to said inner end of said connector housing than said first position wherein said actuator section contacts and moves the free end sections of said first and second spring biased arms apart,
- each of said first and second spring biased arms being biased toward the remaining arm with the free end sections thereof being biased toward engagement with said actuator section.

2. The electrical connector of claim 1 wherein the free end sections of said spring biased arms engage said actuator section and bias said actuator toward said first position.

3. The electrical connector of claim 2 wherein said bottom wall of the connector housing includes an opening spaced from the inner and outer ends of said connector housing to permit said button connector to project into said inner chamber.

4. The electrical connector of claim 3 wherein each of said first and second spring biased arms extends along one side of said opening in said bottom wall of the housing opposite to the remaining spring biased arm, each of said first and second spring biased arms including an arcuately contoured section spaced inwardly of the free end section thereof and positioned adjacent to the opening in said bottom wall, the arcuately contoured sections of said first and second spring biased arms being in opposed alignment and configured to engage and substantially conform to a portion of the peripheral surface of said projecting button connector.

5. The electrical connector of claim 4 wherein said actuator section moves said first and second spring biased arms sufficiently apart in the second position of said actuator to move the arcuately contoured sections of said first and second spring biased arms away from said hole in the bottom wall of said housing, said arcuately contoured sections of said first and second spring biased arms closing to move over a peripheral portion of said hole in the bottom wall of said housing in the first position of said actuator.

6. The electrical connector of claim 5 wherein an electrical lead wire is electrically connected to said first and second spring biased arms, said electrical lead wire extending outwardly from the inner end of said housing.

7. The electrical connector of claim 5 wherein the arcuately contoured section of each said first and second spring biased arm includes a stepped contact surface for contacting peripheral surface of said button connector, said stepped contact surface including a first projecting section for contacting the shank of the button connector, said first projecting section being positioned adjacent to the bottom wall of said housing and a second section recessed from said first projecting section for contacting the enlarged head of said button connector.

8. The electrical connector of claim 7 wherein the bottom wall of said housing is provided with a recessed channel extending from the outer end of said connector housing to the hole in said bottom wall to receive and guide the enlarged head of said button connector.

9. The electrical connector of claim 5 wherein said actuator section includes a cam end surface for engaging and spreading the free end sections of said first and second spring biased arms.

10. The electrical connector of claim 9 wherein each of said first and second spring biased arms includes a cam section formed at the free end section thereof for engaging the cam end surface of said actuator.

11. The electrical connector of claim 10 wherein the cam end surface of said actuator section includes a central apex and first and second inclined surfaces which incline away from said central apex.

12. The electrical connector of claim 6 wherein said first and second spring biased arms are each formed to conduct electrical signals to said electrical lead wire.

13. The electrical connector of claim 6 wherein each of said spring biased arms is mounted for pivotal movement on said housing bottom wall adjacent to the inner end of said housing and a spring electrically connected to said electrical lead wire is mounted in engagement with said first and second spring biased arms to bias said spring biased arms toward one another.

14. Th e electrical connector of claim 13 wherein said spring and said spring biased arms include electrically conductive material to conduct an electrical signal to said electrical lead wire.

15. The electrical connector of claim 14 wherein said spring is a leaf spring, said spring and first and second spring biased arms being coated with a thin layer of electrically conductive metal.

16. The electrical connector of claim 15 wherein said electrically conductive metal is gold.

17. The electrical connector of claim 16 wherein said housing includes a transparent portion to permit visual monitoring of said spring biased arms.

* * * * *